United States Patent
Garrett

(10) Patent No.: US 8,109,914 B2
(45) Date of Patent: Feb. 7, 2012

(54) BEDSIDE CADDY

(76) Inventor: Yvette Garrett, McKinney, TX (US)

( * ) Notice: Subject to any disclaimer, the term of this patent is extended or adjusted under 35 U.S.C. 154(b) by 758 days.

(21) Appl. No.: 12/215,314

(22) Filed: Jun. 26, 2008

(65) Prior Publication Data

US 2008/0319406 A1    Dec. 25, 2008

Related U.S. Application Data

(63) Continuation-in-part of application No. 11/377,144, filed on Mar. 16, 2006, now abandoned.

(51) Int. Cl.
*A61M 1/00* (2006.01)
(52) U.S. Cl. .......................... 604/326; 248/95
(58) Field of Classification Search .......... 604/317–328, 604/367, 408; 248/75, 95, 99, 100, 101, 248/214, 215, 311.3, 318, 328; 383/6, 7, 383/9, 12, 13; 73/215, 219; 211/74, 79, 211/80, 81; 4/144.1, 144.2, 144.3, 144.4; 16/319, 325, 334
See application file for complete search history.

(56) References Cited

U.S. PATENT DOCUMENTS

| | | | | |
|---|---|---|---|---|
| 3,447,536 A | * | 6/1969 | Snyder | 604/348 |
| 3,575,225 A | * | 4/1971 | Muheim | 383/206 |
| 3,872,868 A | | 3/1975 | Kline | |
| 4,126,135 A | * | 11/1978 | Hinman, Jr. | 604/326 |
| 4,295,619 A | * | 10/1981 | Kulin et al. | 248/95 |
| 4,305,405 A | * | 12/1981 | Meisch | 600/575 |
| 4,317,550 A | * | 3/1982 | Hannah | 248/95 |
| 4,393,880 A | * | 7/1983 | Taylor | 600/573 |
| 4,447,939 A | * | 5/1984 | Taylor | 600/580 |
| 4,501,584 A | * | 2/1985 | Cianci et al. | 604/322 |
| 4,562,984 A | * | 1/1986 | Sherlock et al. | 248/95 |
| 4,718,689 A | | 1/1988 | Lott | |
| 4,731,062 A | * | 3/1988 | Gross et al. | 604/322 |
| 4,773,768 A | * | 9/1988 | Leeper | 383/22 |
| 4,938,748 A | | 7/1990 | Yum et al. | |
| 5,375,799 A | * | 12/1994 | Rhodes | 248/95 |
| 5,439,456 A | * | 8/1995 | Fabricant | 604/327 |
| 6,280,425 B1 | * | 8/2001 | Del Guercio | 604/327 |
| 2007/0010797 A1 | * | 1/2007 | Nishtala et al. | 604/540 |

* cited by examiner

*Primary Examiner* — Tatyana Zalukaeva
*Assistant Examiner* — Benedict L Hanrahan
(74) *Attorney, Agent, or Firm* — James Ray & Assoc

(57) ABSTRACT

An apparatus for keeping a urinary container in place while in use. The apparatus comprises a first generally stiff member for positioning between a mattress and box springs of a bed. There is a urinary collection means engageable with and hanging from the first member for retaining urine therein while in use and a fluid communication means engageable with the urinary collection means and with such user for fluid communication of such urine from such user to the urinary collection means.

18 Claims, 3 Drawing Sheets

BEDSIDE CADDY

CROSS REFERENCE TO RELATED APPLICATIONS

This application is a Continuation-in-Part Application and claims priority benefits of patent application Ser. No. 11/377,144 filed Mar. 16, 2006 now abandoned. The teachings of this related application are incorporated herein by reference thereto.

FIELD OF THE INVENTION

The present invention relates, in general, to a urinary or other bodily fluid container, and, more particularly, the present invention relates to a device which keeps such urinary or other bodily fluid bag or container from falling off a bed rail or tipping onto the floor.

BACKGROUND OF THE INVENTION

People that must have catheters, urostomy, ostomies, colostomy or ileostomy (i.e. other bodily fluids) and other such medical devices are constantly at the mercy of these devices. Movement on the bed is restricted and there is a constant problem of pulling on these devices. Sleeping for the patient that is encumbered with one of these devices is difficult because the patient is not free to move about the bed freely.

One other problem with these devices is the possibility of spillage on the bed or on the floor. While another problem is that some medical personnel or care givers are in danger of stepping on the tubing that runs from one of these devices to the bag or container and causing an accident or spilling urine.

Thus, it would be advantageous if there were a device that could be used to assist the patient and the care givers with these medical devices to free both the patient and the care giver from the above listed problems.

SUMMARY OF THE INVENTION

In a first aspect the present invention provides an apparatus for keeping a urinary or other bodily fluid container in place while in use. The apparatus comprises a first generally stiff member for positioning between a mattress and box springs of a bed. There is a urinary collection means engageable with and hanging from the first member for retaining urine therein while in use and a fluid communication means engageable with the urinary collection means and with such user for fluid communication of such urine from such user to the urinary collection means.

OBJECTS OF THE INVENTION

It is, therefore, one of the primary objects of the present invention to provide an apparatus which will keep a urinary or other bodily fluid container or bag in place while the user rests or sleeps.

Another object of the present invention is to provide an apparatus in which a urinary night bag can be used at home.

Still another object of the present invention is to provide an apparatus in which a urinary night bag can be taken anywhere it is needed.

Yet another object of the present invention is to provide an apparatus which will protect the bed and floor from possible spillage of urine or other bodily fluid.

These and various other objects and advantages of this invention will become apparent after a full reading of the following detailed description, particularly, when read in conjunction with the attached drawings as described below and the appended claims.

Figure 1:
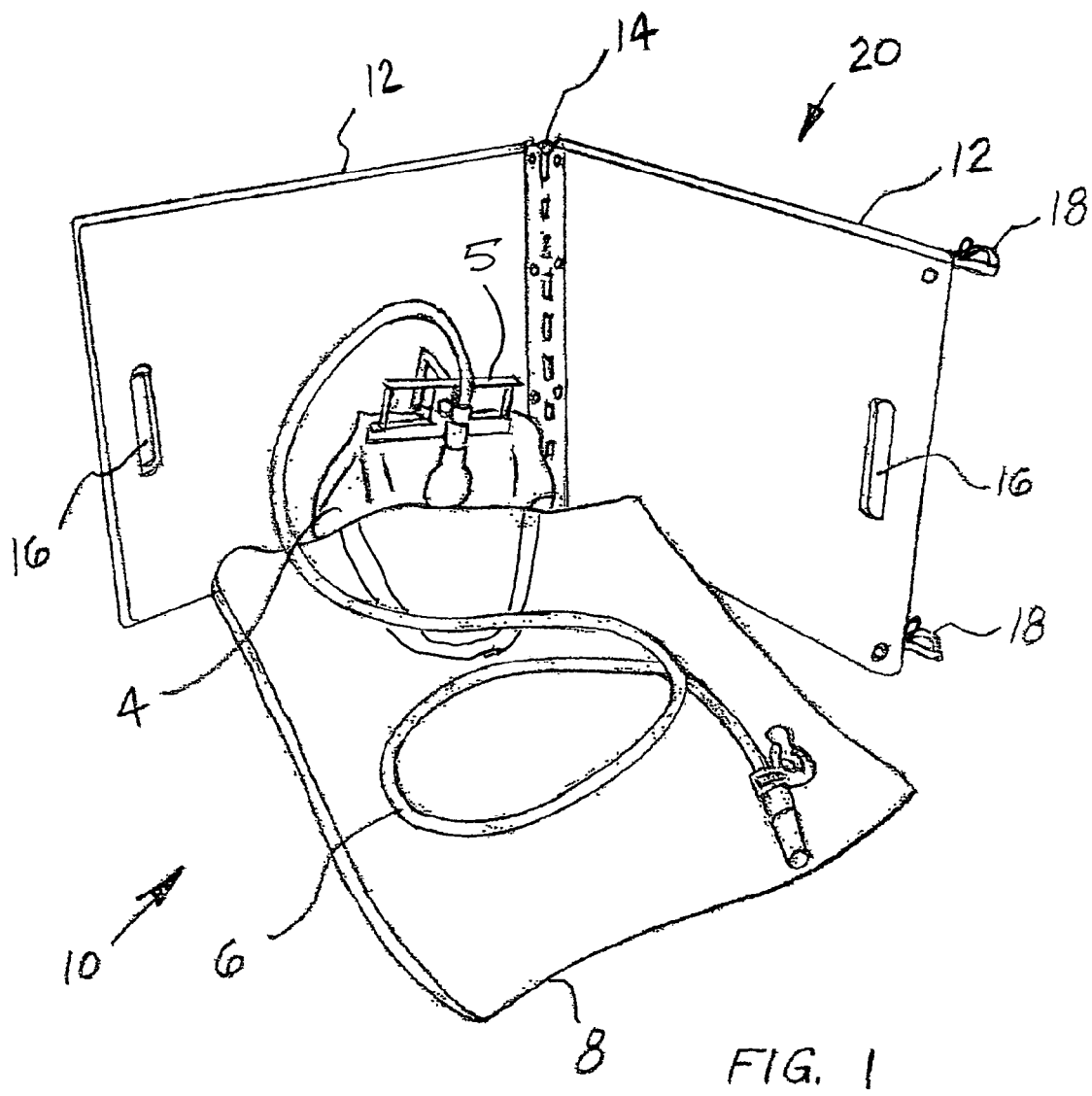
FIG. 1 is a perspective view of the various parts of the apparatus according to an embodiment of the invention.

BRIEF DESCRIPTION OF THE PRESENTLY PREFERRED AND ALTERNATE EMBODIMENTS OF THE INVENTION

Prior to proceeding with the more detailed description of the present invention it should be noted that, for the sake of clarity, identical components which have identical functions have been designated by identical reference numerals throughout the several views illustrated in the drawings.

In a first aspect the present invention provides an apparatus, generally designated 10, for keeping a urinary container in place while in use. The apparatus 10 comprises a generally stiff member 20 for positioning between a mattress and box springs of a bed. Such generally stiff member 20 includes a first generally rectangular stiff member 12 having each of a first predetermined length, a first predetermined width, a first predetermined thickness and formed from a first predetermined material for positioning between a mattress and box springs of a bed. A second generally rectangular stiff member 12 having each of a second predetermined length, a second predetermined width, a second predetermined thickness and formed from a second predetermined material for positioning between a mattress and box springs of a bed. Such first and such second generally rectangular stiff member 12 are substantially identical and therefore, both have the same number. Such two generally rectangular stiff members 12 are also referred to as two substantially identical plate members.

There is a urinary collection means 4 that is engageable with and hanging from one end of the first member 20 for retaining urine therein while in use and a fluid communication means 6 engageable with the urinary collection means 4 and with such user for fluid communication of such urine from such user to the urinary collection means 4.

The above discussion has been described for urinary collection; however, it must be understood that such collection is equally valid for use with other bodily fluids. When used with other bodily fluids such urinary collection bag 4 is replaced with a different bag 4 for such other fluids. Further, it also must also be understood that such collection means 4 and such fluid communication means 6 are normally supplied as a single unit with the bag and tubing as a one piece unit.

As is clearly seen in FIG. 1 such first member 20 is formed of two substantially identical plate members 12 connected to each other by a hinge means 14. Such hinge means is engageable adjacent a first predetermined edge of such generally rectangular stiff member 12 and a confronting edge of the second generally rectangular stiff member 12. The hinge 14 is a continuous hinge 14 that extends across the width of each of the two substantially identical plate members 12.

The two generally rectangular stiff members 12 include a pair of apertures 16, each aperture 16 of the pair of apertures 16 is disposed closely adjacent radially opposed ends of each of two generally rectangular stiff members 12 and can act as carrying handles when said two generally rectangular stiff members 12 are in a folded position.

As stated previously such two plate members 12 are substantially stiff or rigid so that they are secured by positioning between the mattress and box springs. It is presently preferred that such plate members are made of plastic and the preferred plastic is polyurethane.

As stated previously there is a urinary collection means 4 for retaining urine therein while in use. Such urinary collection means 4 is selected from one of a urinary bag and a urinary bottle. It is presently preferred that such collection member 4 is a bag. There is further a fluid communication means 6 that is engageable with the urinary collection means 4 and with such user for fluid communication of such urine from such user to the urinary collection means 4. It is also presently preferred that such fluid communication means 6 is a hose member 6. It is also preferred that such hose member 6 is made of plastic tubing and that such plastic tubing is Tygon tubing (polyvinyl chloride). As stated previously it should be understood that such collection bag 4 and such hose member 6 are generally supplied as a single unit with the bag and tubing as a one piece unit.

Figure 2:
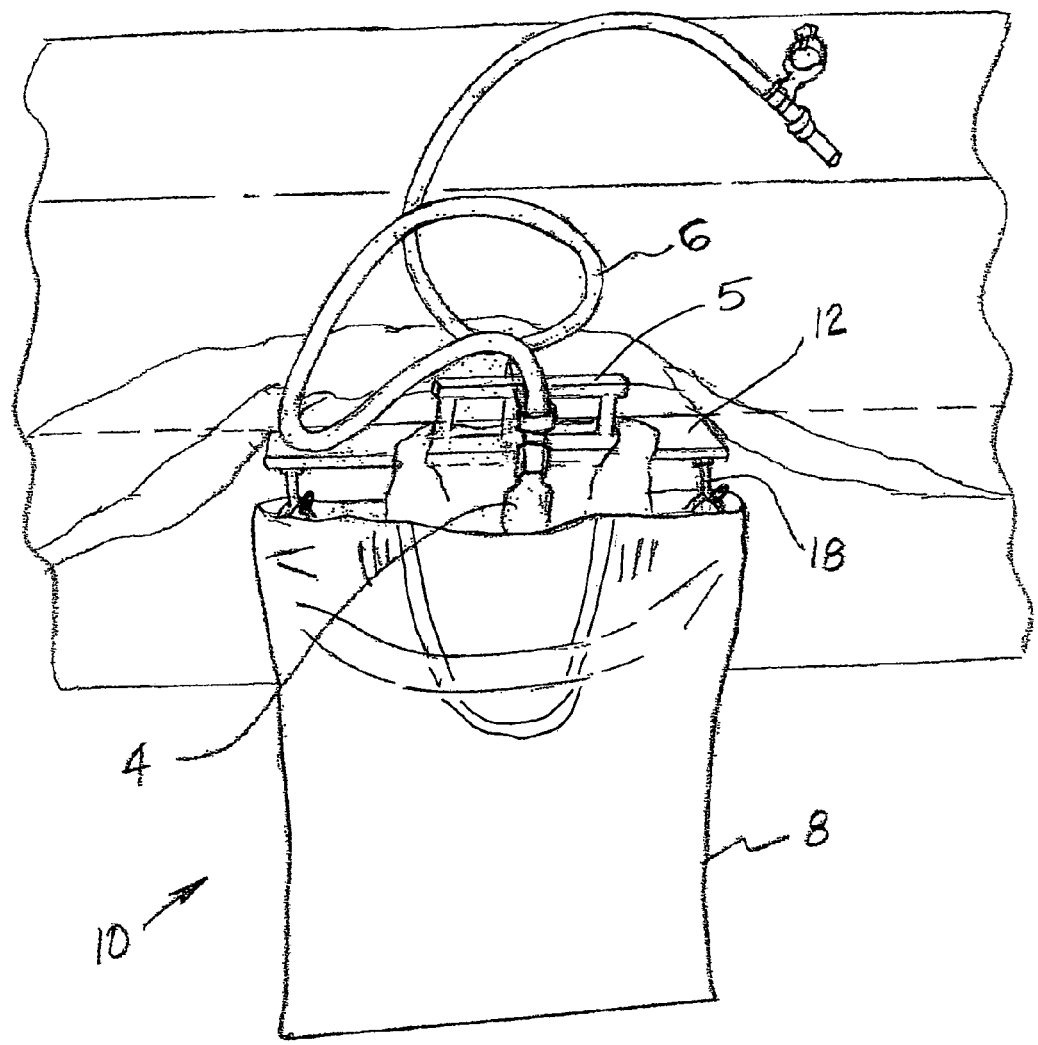
FIG. 2 is a perspective view of the apparatus as it would be in place on the side of a bed.
Figure 3:
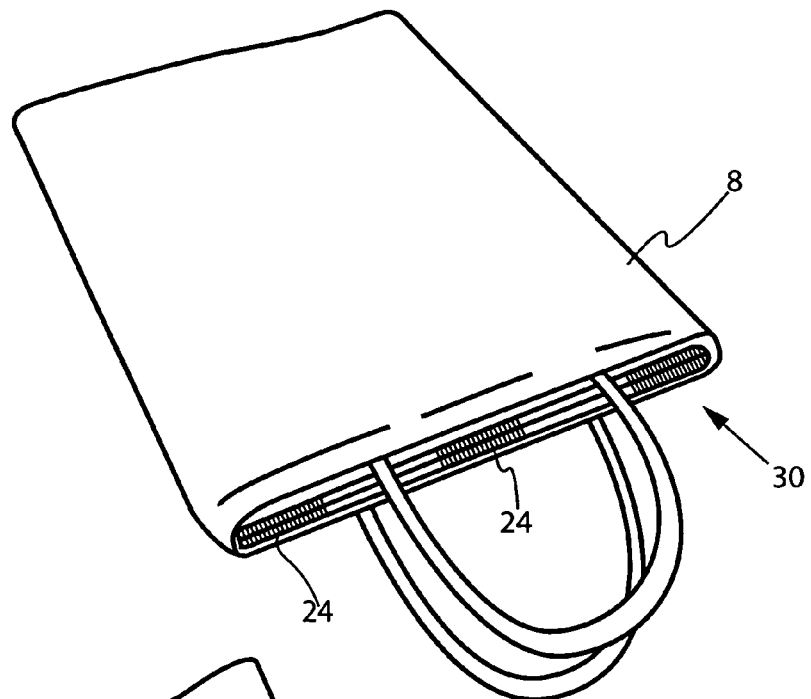
FIG. 3 is a perspective view of the container used to store the apparatus showing such means for closing the container.
Figure 4:
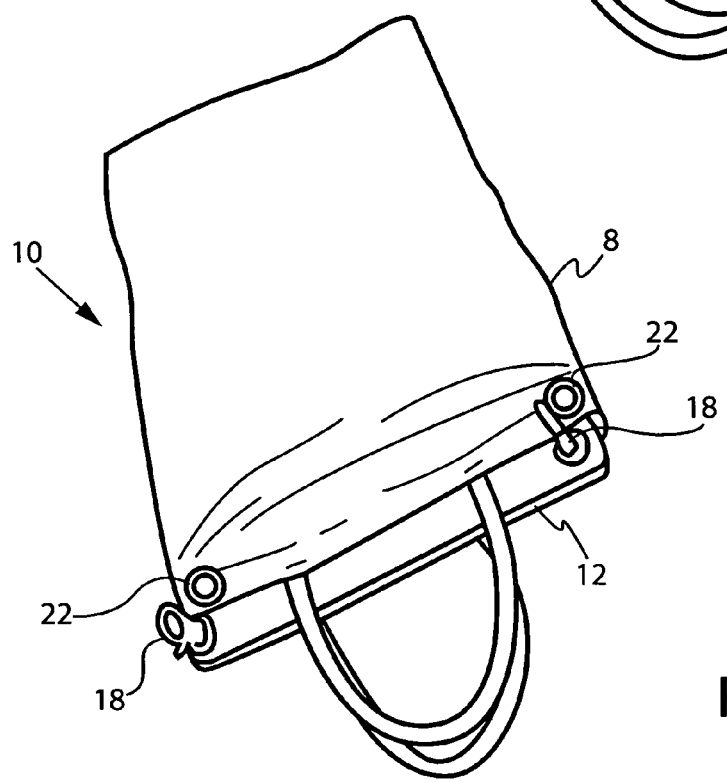
FIG. 4 is a perspective view of the apparatus showing the hooks on the plates of the apparatus for engaging such container.

Such apparatus 10 further includes a means engageable with one such first and such second generally rectangular stiff members 12 for holding such urinary collection means during use. Such means includes the aperture 16 that is also used for engagement with a hanger hook 5 of the urinary collection means 4, as best shown in FIG. 2.

There is a container member 8 that is disposed over the urinary collection means 4 for enclosing from view a primary portion of the urinary collection means 4. There is, further, a pair of attachment means 18 engageable with such one of such first and such second rectangular stiff members 12 and with such container member 8 for holding such container member 8 during use.

Such container member 8 is designed for engagement with first member 20 for enclosing the urinary collection means 4 therein during use. Such container member 8 further acts as a storage container for storing the first member 20, the urinary collection means 4 and the fluid communication means 6 when the apparatus 10 is not in use.

At least one of such first and such second generally rectangular stiff members 12 further includes a pair of hooks 18, each hook 18 of the pair of hooks 18 is disposed on a bottom surface closely adjacent a corner thereof of such one of such first and such second generally rectangular stiff members 12. Such hooks 18 engage and support the container member 8. Such container member 8 further includes a pair of eyelets 22 that are disposed on a top back portion of container member 8 for engagement with the hooks 18 of the generally rectangular stiff members 12 when apparatus 10 is in use.

It is presently preferred that such container member 8 is made of plastic and that such plastic is vinyl. Such container member 8 includes a closure means, generally designated 30, for securing the open end of the container member 8 when such container member 8 has all of the parts of the apparatus disposed therein. It is presently preferred that such closure means 30 includes Velcro® (hook and loop) members 24 disposed on the inside surfaces of the open end of the container member 8. Such closure means 30 may include snaps or other means of closure; however, it is preferred that such closure means 30 be hook and loop members 24 for ease of opening and closing. This is particularly useful for older patients who may not be able to cope with other closure means as easily.

The entire unit can be stored in the container member 8. Such plates 20 fold in half and fit neatly in the container member 8 as does the urinary collection means 4 and the tubing 6. The container member closes and the unit can be taken wherever it is needed and it can be installed in short order.

Thus, the present invention provides an apparatus that can be used at home or taken anywhere it is needed. In addition it can be used when a person is resting or sleeping on a couch. It is designed in particular to keep a urinary container bag in place when a person is sleeping or resting. The apparatus keeps the urinary night bag or container from falling off the bed rail or tipping over onto the floor. It also helps to keep the user from pulling on the urostomy bag, catheter or other device and allows the user to move more freely in bed while sleeping. In addition it adds more length to the tubing attached to the bag. The apparatus 10 will keep the urinary bag clean and sanitary as well as protecting the floor and bedding from possible spillage. Moreover, it will prevent others from inadvertently stepping on the tubing. While a presently preferred embodiment and alternate embodiments of the present invention has been described in detail above, it should be understood that various other adaptations and/or modifications of the invention can be made by those persons who are particularly skilled in the art without departing from either the spirit of the invention or the scope of the appended claims.

I claim:

1. An apparatus for keeping a urinary container in place while in use, said apparatus comprising:
   (a) a first generally rectangular stiff member having each of a first predetermined length, a first predetermined width, a first predetermined thickness and formed from a first predetermined material for positioning between a mattress and box springs of a bed;
   (b) a second generally rectangular stiff member having each of a second predetermined length, a second predetermined width, a second predetermined thickness and formed from a second predetermined material for positioning between a mattress and box springs of a bed;
   (c) a hinge engageable adjacent a first predetermined edge of said first generally rectangular stiff member and a confronting edge of said second generally rectangular stiff member, whereby said first and said second generally rectangular stiff members are disposed in a generally planar unfolded position when positioned between the mattress and the box springs of the bed and whereby said first and said second generally rectangular stiff members are disposed in a folded position;
   (d) a urinary collection means for retaining urine therein while in use;
   (e) a means for holding said urinary collection means adjacent a side of the bed when said first and second generally rectangular stiff members are positioned between the mattress and the box springs of the bed;
   (f) a container member disposed over said urinary collection means for enclosing from view a primary portion of said urinary collection means;
   (g) a pair of attachment means for holding said container member in a suspended position during use of said urinary collection means when said first and second generally rectangular stiff members are positioned between the mattress and the box springs of the bed; and (h) a fluid communication means engageable with said urinary collection means and with such user for fluid communication of such urine from such user to said urinary collection means.

2. The apparatus, according to claim 1, wherein said second generally rectangular stiff member is substantially identical to said first generally rectangular stiff members.

3. The apparatus, according to claim 1, wherein said hinge is a continuous hinge extending across a width of each of said two substantially identical generally rectangular stiff members.

4. The apparatus, according to claim 1, wherein said means for holding said urinary collection means adjacent the side of the bed includes a pair of apertures, each aperture of said pair of apertures disposed closely adjacent radially opposed edges of each of said two substantially identical generally rectangular stiff members and further adapted as carrying handles when said two substantially identical generally rectangular stiff members are in said folded position.

5. The apparatus, according to claim 2, wherein said two substantially identical generally rectangular stiff members are formed of plastic.

6. The apparatus, according to claim 5, wherein said plastic is polyurethane.

7. The apparatus, according to claim 1, wherein said urinary collection means is selected from one of a urinary bag and a urinary bottle.

8. The apparatus, according to claim 7, wherein said urinary collection means is a urinary bag.

9. The apparatus, according to claim 1, wherein said fluid communication means is a hose member.

10. The apparatus, according to claim 9, wherein said hose member is made of plastic.

11. The apparatus, according to claim 1, wherein said container member for engagement with said one of said first and said second generally rectangular stiff members for enclosing said urinary collection means therein.

12. The apparatus, according to claim 1, wherein said container member further acts as a storage container for one of storing and transporting said two substantially identical generally rectangular stiff members, said urinary collection means and said fluid communication means when said apparatus is not in use.

13. The apparatus, according to claim 12, wherein said apparatus is completely portable.

14. The apparatus, according to claim 1, wherein said container member is made of vinyl.

15. The apparatus, according to claim 1, wherein said container member includes a closure means for securing an open end of said container member.

16. The apparatus, according to claim 15, wherein said closure means includes hook and loop members disposed on inside surfaces of said open end of said container member.

17. The apparatus, according to claim 1, wherein said pair of attachment means for holding said container member in position during use includes a pair of hooks, each hook of said pair of hooks is disposed on a bottom surface closely adjacent a corner of said one of said first and said second generally rectangular stiff members positioned between the mattress and the box spring of the bed, said pair of hooks further positioned adjacent an edge being opposite to said first predetermined edge.

18. The apparatus, according to claim 17, wherein said container member further includes a pair of eyelets disposed on a top back portion of said container member for engagement with said hooks disposed on one of said two substantially identical generally rectangular stiff members when said apparatus is in use.

* * * * *